(12) United States Patent
Abraham et al.

(10) Patent No.: US 10,898,268 B2
(45) Date of Patent: Jan. 26, 2021

(54) OVERLAY IMAGING FOR REGISTRATION OF A PATIENT EYE FOR LASER SURGERY

(71) Applicant: Novartis AG, Basel (CH)

(72) Inventors: Mario Abraham, Burgthann (DE);
Michael Wittnebel, Hirschaid (DE);
Matthias Stehr, Wörthsee (DE)

(73) Assignee: Alcon Inc.

( * ) Notice: Subject to any disclaimer, the term of this patent is extended or adjusted under 35 U.S.C. 154(b) by 102 days.

(21) Appl. No.: 16/097,800

(22) PCT Filed: May 2, 2016

(86) PCT No.: PCT/IB2016/052496
§ 371 (c)(1),
(2) Date: Oct. 30, 2018

(87) PCT Pub. No.: WO2017/191487
PCT Pub. Date: Nov. 9, 2017

(65) Prior Publication Data
US 2019/0151024 A1    May 23, 2019

(51) Int. Cl.
*A61B 34/10* (2016.01)
*A61F 9/008* (2006.01)
*A61B 3/117* (2006.01)
*A61B 34/00* (2016.01)
*A61B 90/00* (2016.01)
*G06T 7/33* (2017.01)
*G06T 3/60* (2006.01)

(52) U.S. Cl.
CPC .............. *A61B 34/10* (2016.02); *A61B 3/117* (2013.01); *A61B 34/25* (2016.02); *A61B 90/39* (2016.02); *A61F 9/008* (2013.01); *G06T 3/60* (2013.01); *G06T 7/337* (2017.01); *A61B 2034/105* (2016.02); *A61B 2090/3937* (2016.02); *A61B 2090/3983* (2016.02); *A61B 2090/3995* (2016.02); *A61F 2009/00878* (2013.01); *G06T 2207/10024* (2013.01); *G06T 2207/20221* (2013.01); *G06T 2207/30041* (2013.01); *G06T 2207/30204* (2013.01)

(58) Field of Classification Search
None
See application file for complete search history.

(56) References Cited

U.S. PATENT DOCUMENTS

2003/0223037 A1* 12/2003 Chernyak .......... A61F 9/00806
351/209
2007/0055222 A1   3/2007 Hohla et al.
(Continued)

FOREIGN PATENT DOCUMENTS

CN    1650148 A    8/2005
EP    1800636 A1 *  6/2007  ............... A61G 9/01
(Continued)

*Primary Examiner* — Leon Viet Q Nguyen (57) ABSTRACT

Methods and systems for overlay imaging for registration of a patient eye for laser surgery include aligning and overlaying a surgical image of the limbus over a previously acquired diagnostic image of the limbus. The surgical image is displayed with a degree of transparency and enabled to rotate about the limbus center. Various types of colors, markers, contrast, and backgrounds may be used to generate a display for determining the alignment angle between the diagnostic image and the surgical image.

20 Claims, 5 Drawing Sheets

(56) References Cited

U.S. PATENT DOCUMENTS

| | | | |
|---|---|---|---|
| 2007/0142826 A1 | 6/2007 | Sacharoff | |
| 2014/0125949 A1* | 5/2014 | Shea | A61B 3/0025 |
| | | | 351/206 |
| 2016/0113727 A1* | 4/2016 | Tripathi | A61B 3/14 |
| | | | 606/107 |

FOREIGN PATENT DOCUMENTS

| | | |
|---|---|---|
| EP | 1800636 A1 | 6/2007 |
| IE | 102010046500 A1 | 3/2012 |
| JP | 2006522629 A | 10/2006 |
| WO | 2015/043616 A1 | 4/2015 |
| WO | 2016/061454 A1 | 4/2016 |

* cited by examiner

OVERLAY IMAGING FOR REGISTRATION OF A PATIENT EYE FOR LASER SURGERY

BACKGROUND

Field of the Disclosure

The present disclosure relates to ophthalmic surgery, and more specifically, to overlay imaging for registration of a patient eye for laser surgery.

Description of the Related Art

In ophthalmology, eye surgery, or ophthalmic surgery, saves and improves the vision of tens of thousands of patients every year. However, given the sensitivity of vision to even small changes in the eye and the minute and delicate nature of many eye structures, ophthalmic surgery is difficult to perform and the reduction of even minor or uncommon surgical errors or modest improvements in accuracy of surgical techniques can make an enormous difference in the patient's vision after the surgery.

Ophthalmic surgery is performed on the eye and accessory visual structures. More specifically, various types of laser ablation surgery (or simply 'laser surgery') may be performed on the cornea, lens, or other structures in the eye for clinical treatment purposes. Typically, prior to laser surgery a diagnostic image of the eye is acquired to characterize the eye and to identify specific treatment locations, among other uses. Subsequently, when the laser surgery is initiated on the eye using a surgical laser system, an initial step in the surgery is registration of the eye to confirm the identity of the patient and to correlate the eye to the diagnostic image. Typical surgical laser systems display the diagnostic image next to a surgical image of the eye being acquired for registration purposes. During registration, the surgeon or other medical personnel may find that precise rotational alignment of the eye using the two images displayed next to one another, the diagnostic image and the surgical image, is difficult or time-consuming.

SUMMARY

In one aspect a disclosed method is for registration of patient eyes for ophthalmic surgery. The method may include acquiring a surgical image including the limbus of a patient eye subject to ophthalmic surgery, and overlaying the surgical image on a diagnostic image including the limbus, the diagnostic image being previously acquired from the patient eye. The method may also include aligning a first limbus center of the surgical image with a second limbus center of the diagnostic image, and displaying the surgical image being rotated about the first limbus center over an angular range. In the method, the surgical image may have a transparency enabling simultaneous viewing of the surgical image and the diagnostic image during at least a portion of the angular range. In the method, the angular range may include an alignment angle for the surgical image at which the surgical image and the diagnostic image are cyclotorsonally aligned with respect to the first limbus center and the second limbus center, respectively.

In any of the disclosed embodiments of the method, the surgical image and the diagnostic image may include at least a portion of the iris of the patient's eye.

In any of the disclosed embodiments of the method, both the surgical image and the diagnostic image may respectively include at least one identical marker at a common location with respect to the iris of the patient's eye. In the method, the marker may be an indication of an iris structure of the iris displayed over a uniform background in place of the iris. In the method, a first marker of the surgical image has a first color, and a second marker of the diagnostic image has a second color. In the method, the marker may have a hollow shape. In the method, the hollow shape may include at least one of a polygon and an ellipse.

In any of the disclosed embodiments of the method, displaying the surgical image may further include displaying the surgical image being incrementally rotated about the first limbus center over a step angle of rotation, in response to user input indicating the step angle.

In any of the disclosed embodiments, the method may further include receiving user input specifying the alignment angle, displaying the surgical image rotated about the first limbus center at the alignment angle, and varying the transparency of the surgical image from low transparency to high transparency.

In any of the disclosed embodiments, the method may further include receiving user input to select at least one of the displayed transparency, the range of transparency from high transparency to low transparency, a step transparency within the transparency range, a first color in the surgical image, a second color in the diagnostic image, a number of markers, a type of marker, a location of a marker, a contrast of the iris, a displayed portion of the iris, the angular range, and a step angle within the angular range.

Another disclosed aspect includes an image processing system for overlay imaging for registration of a patient eye for ophthalmic surgery, the image processing system including a processor enable to access memory media storing instructions executable by the processor to perform the method, or any portions thereof. A further disclosed aspect includes an article of manufacture comprising non-transitory memory media for characterizing membranes at vitreoretinal interfaces, the memory media storing instructions executable by a processor to perform the method, or any portions thereof.

BRIEF DESCRIPTION OF THE DRAWINGS

For a more complete understanding of the present invention and its features and advantages, reference is now made to the following description, taken in conjunction with the accompanying drawings, in which.

DESCRIPTION OF PARTICULAR EMBODIMENT(S)

In the following description, details are set forth by way of example to facilitate discussion of the disclosed subject matter. It should be apparent to a person of ordinary skill in the field, however, that the disclosed embodiments are exemplary and not exhaustive of all possible embodiments.

As used herein, a hyphenated form of a reference numeral refers to a specific instance of an element and the un-hyphenated form of the reference numeral refers to the collective element. Thus, for example, device '12-1' refers to an instance of a device class, which may be referred to collectively as devices '12' and any one of which may be referred to generically as a device '12'.

As noted above, registration of a patient's eye is performed as an initial step during various types of ophthalmic surgery. In particular, for laser surgery of the cornea or eye lens, an image of the limbus of the eye may be acquired during diagnosis, referred to as a 'diagnostic image'. The diagnostic image may be used, along with other acquired data and measurements, to determine a treatment plan for the eye, such as a surgical plan for the laser surgery. When the patient is prepared for the laser surgery and is positioned within the laser surgery system, a 'surgical image' of the patient's eye, including the limbus, is acquired and used for registration of the eye. The registration using the surgical image serves to identify the patient and to confirm that the correct eye is undergoing laser surgery.

Additionally, because cyclotorsion of the eye may occur to some degree, registration may further involve a precise rotational alignment of the eye with respect to the diagnostic image. Because the ability to rotate the patient may be limited, an alignment angle may be determined by the surgical laser system representing a slight rotational (angular) offset between the diagnostic image and the surgical image. The alignment angle may then be recorded by the surgical laser system and used to rotationally offset laser activity on the eye accordingly. The alignment angle is generally measured about a rotation point that is the geometric center of the limbus, which provides a more stable rotational alignment point than the center of the pupil, which can change as the pupil size changes. To the extent that the pupil diameter is somewhat comparable in each of the images, the limbus also provides a stable circular structure that can be used for precise scaling alignment of the diagnostic image to the surgical image, even when the two images differ in size, resolution, color, and wavelength of light used, among other aspects.

Because the precise rotational alignment of the eye is crucial for properly performing the surgical plan for the laser surgery, the surgeon or other surgical personnel will typically verify that the alignment angle determined has a high degree of accuracy. Thus, the checking and confirmation of the alignment angle may represent an important operation during registration of the eye for the laser surgery.

Conventional surgical laser systems are typically equipped to provide the diagnostic image next to the surgical image on a display screen that is viewed by an operator of the surgical laser system, often the surgeon or other surgical personnel. The surgical image may be acquired using microscope optics and a camera that is included with the surgical laser system. However, determining the alignment angle between the diagnostic image and the surgical image when the two images are displayed next to one another may be difficult and time consuming, because such an arrangement may be challenging for human visual cognition to interpret. Thus, by virtue of the side-by-side arrangement found in conventional surgical laser systems, the overall accuracy of the alignment angle determined in this manner may be limited, which is undesirable because it represents a potential source of error for performing the surgical plan.

As will be described in further detail herein, the inventors of the present disclosure have provided methods and systems of overlay imaging for registration of a patient eye for laser surgery. Instead of presenting the diagnostic image next to the surgical image during registration, the methods and systems of overlay imaging for registration of a patient eye disclosed herein may display the two images as a single overlay image comprised of the surgical image superimposed on the diagnostic image. The methods and systems of overlay imaging for registration of a patient eye disclosed herein may further provide a variable degree of transparency, from low transparency to high transparency, of the surgical image. The methods and systems of overlay imaging for registration of a patient eye disclosed herein may align the diagnostic image and the surgical image based on the limbus in each respective image, and may enable rotation of the surgical image relative to the diagnostic image about the limbus center. The methods and systems of overlay imaging for registration of a patient eye disclosed herein may also enable displaying the surgical image being rotated relative to the underlying diagnostic image about the limbus center. For example, the surgical image may be rotated about an angular range that includes the alignment angle, such as with a video loop created with individual frames at individual step angles of the rotation, to allow human visual cognition to more accurately and precisely determine or verify the alignment angle. The methods and systems of overlay imaging for registration of a patient eye disclosed herein may still further provide markers that are indicative of certain structures in the eye, such as iris structures that are unique to the eye. Other geometric markers, such as polygons or ellipses, may also be used. The methods and systems of overlay imaging for registration of a patient eye disclosed herein may enable selection and configuration by users of various features for flexible and customizable displays for determining and verifying the alignment angle. The methods and systems of overlay imaging for registration of a patient eye disclosed herein may be implemented using an image processing system that is included with or that operates with the surgical laser system.

Figure 1A:
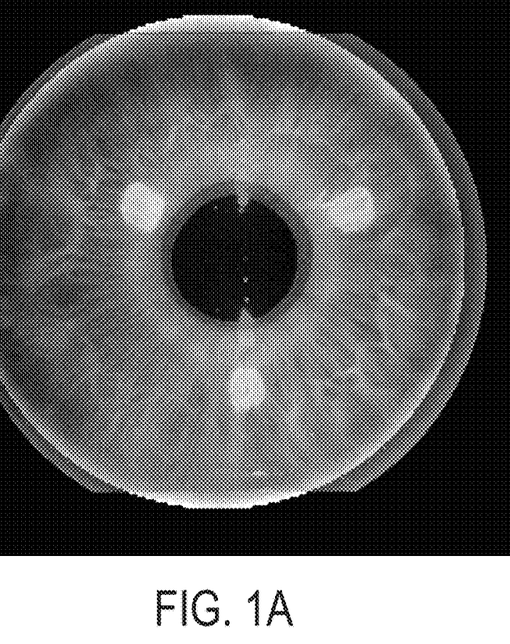
FIGS. 1A and 1B show an embodiment of overlay imaging for registration of a patient eye depicting the iris.
Figure 1B:
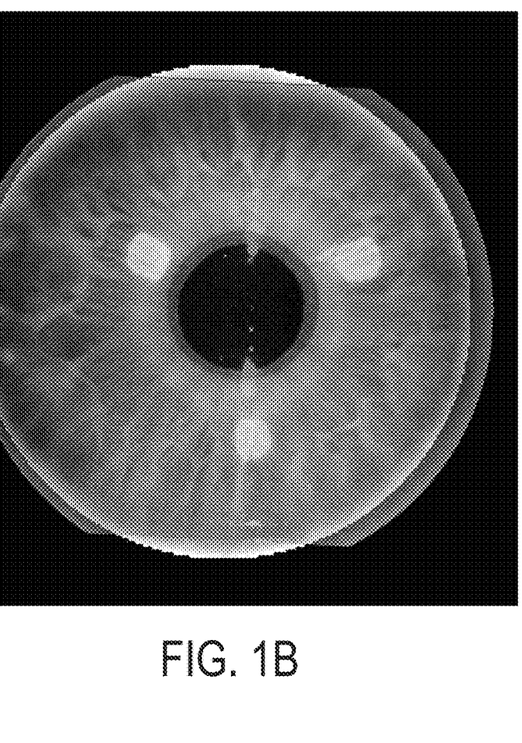

Referring now to the drawings, FIGS. 1A and 1B show an embodiment of overlay imaging for registration of a patient eye depicting the iris. In FIGS. 1A and 1B overlay images comprising a diagnostic image (lower or back image) over which a surgical image (upper or front image) has been superimposed and aligned at the limbus center of each respective image. In FIGS. 1A and 1B, substantially all of the iris structure as well as the pupil is shown in both the diagnostic image and the surgical image, where the pupil is slightly larger in the diagnostic image as compared to the surgical image. As shown, FIG. 1A shows a first overlay image that is slightly out of rotational alignment, while FIG. 1B shows a second overlay image that is more precisely aligned, as evident by the improved sharpness of the iris structures visible. In FIG. 1B, the more sharp alignment is visible in the clarity of the iris structures, particularly as compared with FIG. 1A. Accordingly, the image shown in FIG. 1B may represent an optimal alignment for cyclotorsion about the limbus center between the diagnostic image and the surgical image, and the alignment angle may be determined, or estimated, from the angular offset applied in FIG. 1B, which is known.

As shown, the images in FIGS. 1A and 1B represent examples of overlay imaging for registration of a patient eye, as disclosed herein. Accordingly, the overlay images shown in FIG. 1A and FIG. 1B may be displayed in a variety of different manners and techniques, as described herein. Because the overlay images shown in FIG. 1A and FIG. 1B may be generated and displayed using an image processing system (see FIG. 4), both the diagnostic image and the surgical image may be processed and displayed as digital images, allowing for various types of manipulation. For example, user input may be received to determine the actual angular offset displayed, allowing a user to manually determine the optimal alignment angle for cyclotorsion by 'tuning' the offset angle, as desired. In some embodiments, user input may be received to determine a step angle of rotation for rapid bidirectional manual rotation. Although only static images can be displayed in the drawings, it will be appreciated that a dynamic, or animated, view of the images shown in FIGS. 1A and 1B may be generated by varying an offset angle of the surgical image relative to the diagnostic image. In various embodiments, the offset angle may be varied over an angular range about the limbus center that includes the alignment angle, or the expected alignment angle. The display of the offset angle over the angular range may be repeated in a loop with bidirectional rotation. In this manner, a user may be able to confirm with a high degree of certainty, accuracy, and precision that the alignment angle selected is actually the optimal alignment angle. The animation loop about the angular range described above may be activated or repeated, for example, when the alignment angle has been tentatively determined in a first iteration, to enable determination of the alignment angle with increased, or optimal, accuracy in degrees of rotation, such as limited by the resolution of the raw image data or limited by the processing ability of the surgical laser system or the image processing system.

It is further noted that color and contrast may be varied (not shown) for the diagnostic image or the surgical image or both. For example, the diagnostic image may be a first color, while the surgical image may be a second color. When both images are aligned, the resulting image may accordingly appear as a third color that is a combination of the first color and the second color.

Other types of displays may also be generated, as described herein. For example, a transparency of the overlaid surgical image may be varied (not shown) between low transparency (mostly or all opaque) to high transparency (mostly or all transparent). The transparency of the surgical image may be varied manually by the user, such as by user input specifying the transparency. As an animation, the transparency of the surgical image may be automatically varied from low transparency to high transparency. The user may be enabled to determine the speed of the animation, as well as the transparency levels corresponding to low transparency and high transparency, respectively. In this manner, the animation may transition from the diagnostic image to the surgical image without a change in the offset angle between the two images, to provide another view that enables highly precise and accurate determination of the alignment angle by more clearly presenting misaligned features in the display output to the user. As with the other techniques for overlay imaging disclosed herein, the transparency animation may enable determination of the optimal alignment angle that appears best aligned in various different overlay displays.

Still further, as will be shown in the subsequent figures, certain portions of the overlay image may be masked out or covered with a solid region, instead of the entire image within the limbus, for clarity and visual simplicity. Various types of markers may be used in the overlay image, such as, but not limited to, iris markers that are indicative of particular iris structures, and geometric markers, such as a polygon or an ellipse, which may also be hollow markers for improved recognition of alignment. The number, type, location, size, among other features of the markers may be user selectable. The markers may include optical markers, such as regions of varied illumination, brightness, contrast, or other optical image property.

Figures 2A, 2B, 2C:
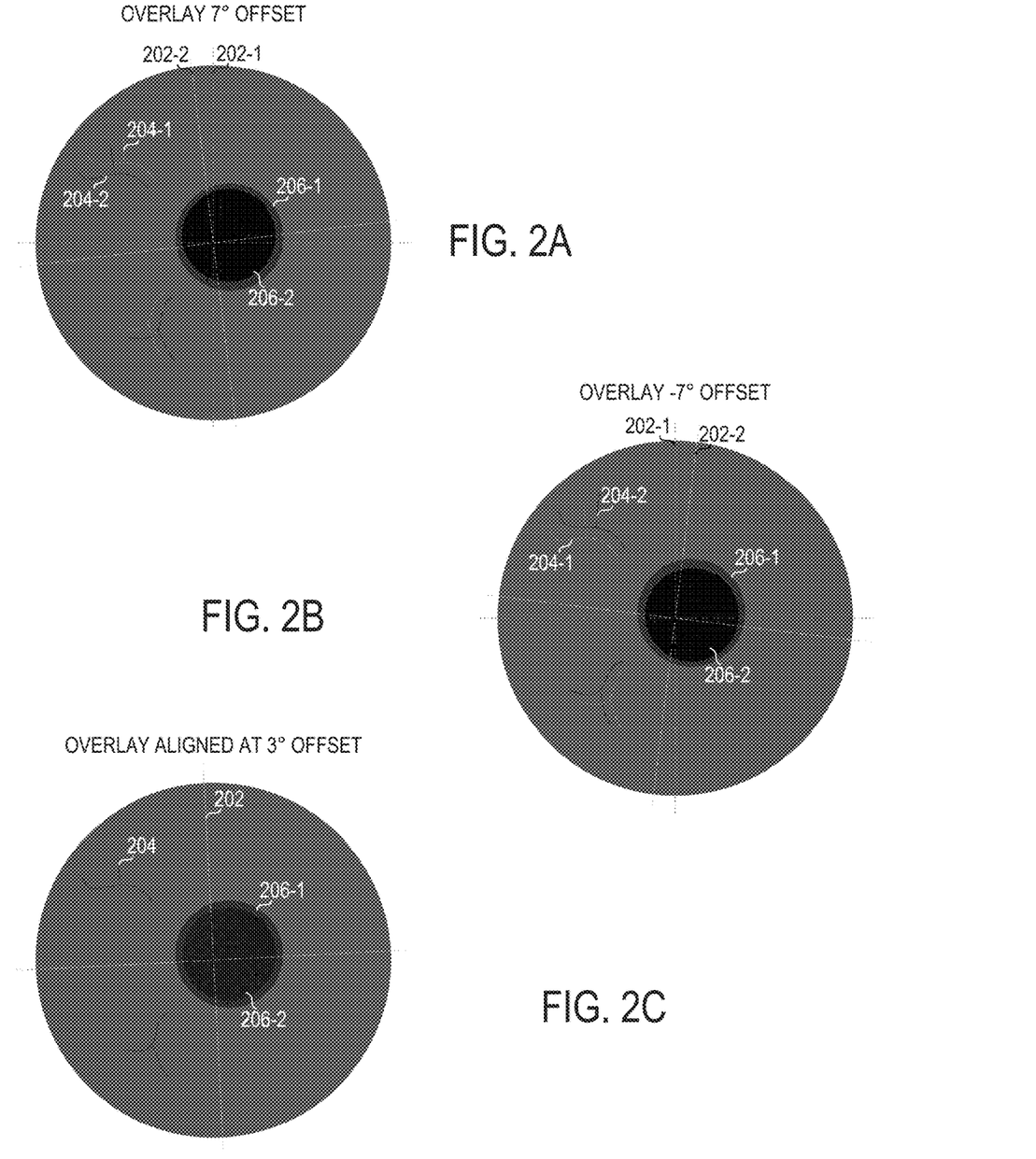
FIGS. 2A, 2B, and 2C shows an embodiment of overlay imaging for registration of a patient eye using iris markers.

Referring now to FIGS. 2A, 2B, and 2C, an embodiment of overlay imaging for registration of a patient eye depicting the iris using iris markers 204 is shown. Iris markers 204 may be indicative of a particular feature in the iris of the eye (see FIGS. 1A and 1B). In FIGS. 2A, 2B, and 2C overlay images for the limbus are shown indicative of a diagnostic image (lower or back image) respectively superimposed over a surgical image (upper or front image) and aligned at the limbus center of each respective image. In FIGS. 2A, 2B, and 2C, the image of the iris has been replaced with a uniform ring field for greater optical clarity in viewing iris markers 204. In FIGS. 2A, 2B, and 2C, a first pupil 206-1 pupil is shown for the diagnostic image and a second pupil 206-2 is shown for the surgical image, where first pupil 206-1 is slightly larger than second pupil 206-2. It is noted that in other embodiments, first pupil 206-1 and second pupil 206-2 may be the same size or different sizes, and the pupil size may be modulated by adjusting the illumination on the eye. In FIGS. 2A, 2B, and 2C, a first reticle 202-1 is also shown for the diagnostic image and a second reticle 202-2 is shown for the surgical image. Reticles 202 cross at a common point that is the limbus center, which is not affected by a change in size of pupils 206. As shown, FIG. 2A shows a third overlay image that has an angular offset of 7° about the limbus center and is accordingly out of rotational alignment, FIG. 2B shows a fourth overlay image that has an angular offset of −7° about the limbus center and is accordingly out of rotational alignment. The diagnostic image having reticle 202-1 is shown at alignment with vertical and horizontal. FIG. 2C shows a fifth overlay image that is more precisely aligned, albeit at an offset of 3° from vertical or horizontal.

In FIG. 2A, iris marker 204-2 is offset from iris marker 204-1, and may be more clearly visible that an actual picture of the iris that iris markers 204 represent. Iris markers 204 may be generated using the same image processing operation from a respective iris image. In FIG. 2B, iris marker 204-2 is offset in an opposite direction from iris marker 204-1 as compared to FIG. 2A. In FIG. 2C, iris markers 204 appear as singular markers due to the precise alignment in the overlay image, and reticle 202 also appears as a single reticle.

As with FIGS. 1A and 1B, it is noted that various different modifications and techniques may be used with the overlay images shown in FIGS. 2A, 2B, and 2C. In some embodiments, certain portions of the iris may be blended in with a varying degree of transparency, as described above. Iris markers 204 may be shown along with the actual iris structure represented by iris markers 204, or any desired portion thereof. Color and transparency of any of the image elements shown or described may be varied manually or automatically in an animation loop, as described above, with user configuration of various display parameters relating to color, time, transparency, among others. In particular, when an offset angle of the diagnostic image is not aligned with vertical or horizontal, the alignment angle may be determined relative to any offset angle of the diagnostic image, as shown in FIG. 2C.

Figure 3A:
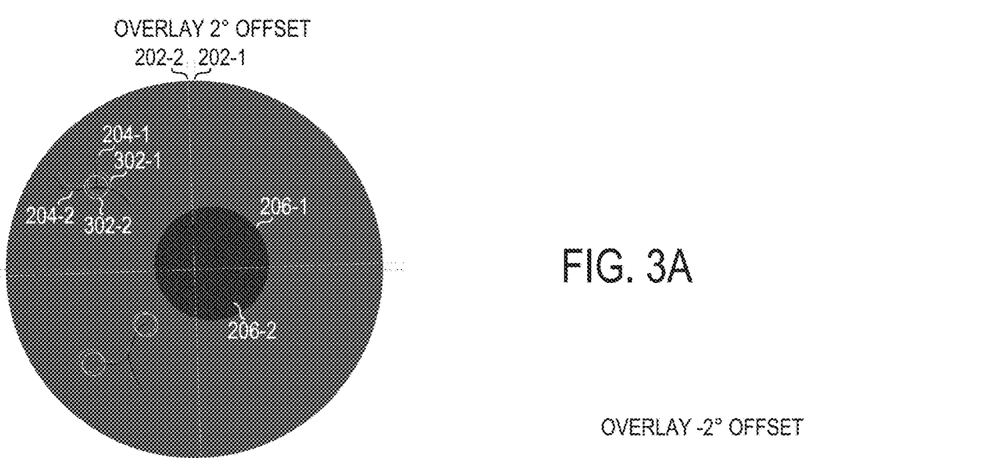
FIGS. 3A, 3B, and 3C shows an embodiment of overlay imaging for registration of a patient eye using iris markers and shape markers.
Figures 3B, 3C:
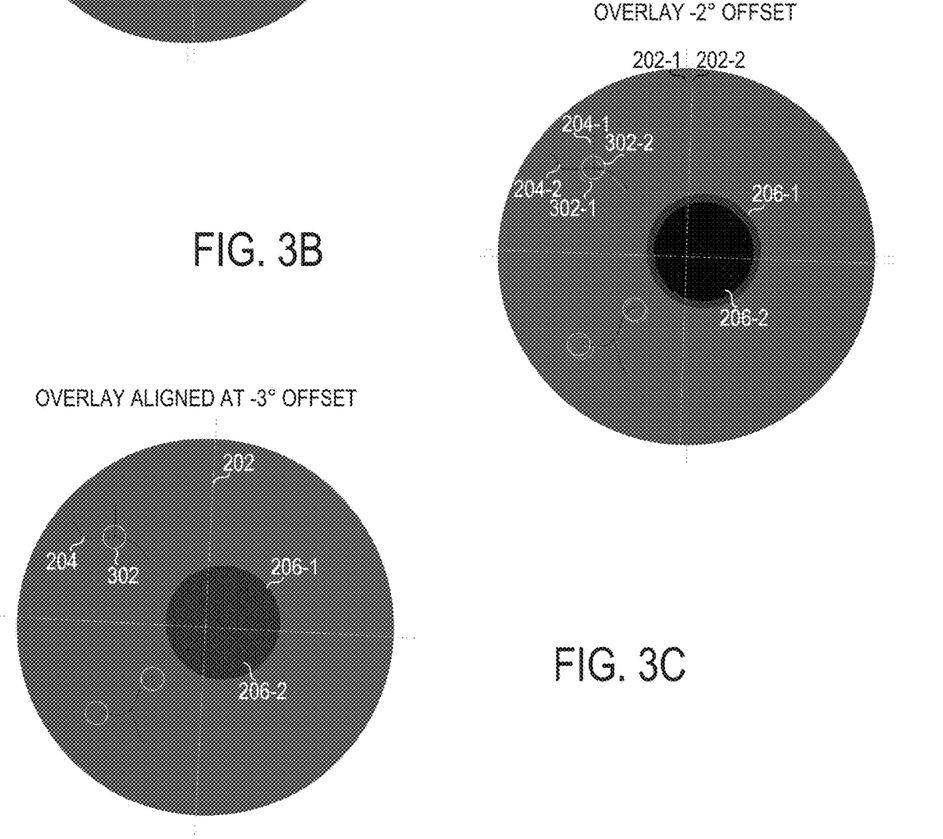

Referring now to FIGS. 3A, 3B, and 3C, an embodiment of overlay imaging for registration of a patient eye depicting the iris using iris markers 204 and geometric markers 302. Iris markers 204 may be indicative of a particular feature in the iris of the eye (see FIGS. 1A and 1B) and are the same as described above with respect to FIGS. 2A, 2B, and 2C. In FIGS. 3A, 3B, and 3C, overlay images for the limbus are shown indicative of a diagnostic image (lower or back image) respectively superimposed over a surgical image (upper or front image) and aligned at the limbus center of each respective image. In FIGS. 3A, 3B, and 3C, the image of the iris has been replaced with a uniform ring field for greater optical clarity in viewing iris markers 204 and geometric markers 302. In FIGS. 3A, 3B, and 3C, a first pupil 206-1 pupil is shown for the diagnostic image and a second pupil 206-2 is shown for the surgical image, where first pupil 206-1 is slightly larger than second pupil 206-2. In FIGS. 3A, 3B, and 3C, a first reticle 202-1 is also shown for the diagnostic image and a second reticle 202-2 is shown for the surgical image. Reticles 202 cross at a common point that is the limbus center, which is not affected by a change in size of pupils 206. As shown, FIG. 3A shows a sixth overlay image that has an angular offset of 2° about the limbus center and is accordingly out of rotational alignment, FIG. 3B shows a seventh overlay image that has an angular offset of −2° about the limbus center and is accordingly out of rotational alignment. The diagnostic image having reticle 202-1 is shown at alignment with vertical and horizontal. FIG. 3C shows an eighth overlay image that is more precisely aligned, albeit at an offset of −3° from vertical or horizontal.

In FIGS. 3A, 3B, and 3C, geometric markers 302 are shown as circles, which is a special case of an ellipse more generally. Geometric markers 302 are further shown as hollow markers, which may enable a more precise or accurate alignment over the entire marker, as well as over the visible portion from the hollow space of the underlying image (here iris markers 204). In FIGS. 3A, 3B, and 3C, geometric marker 302-1 is in the diagnostic image, while geometric marker 302-2 is in the surgical image. As with the previous figures described in detail above, it is noted that various different modifications and techniques may be used with the overlay images shown in FIGS. 3A, 3B, and 3C.

Figure 4:
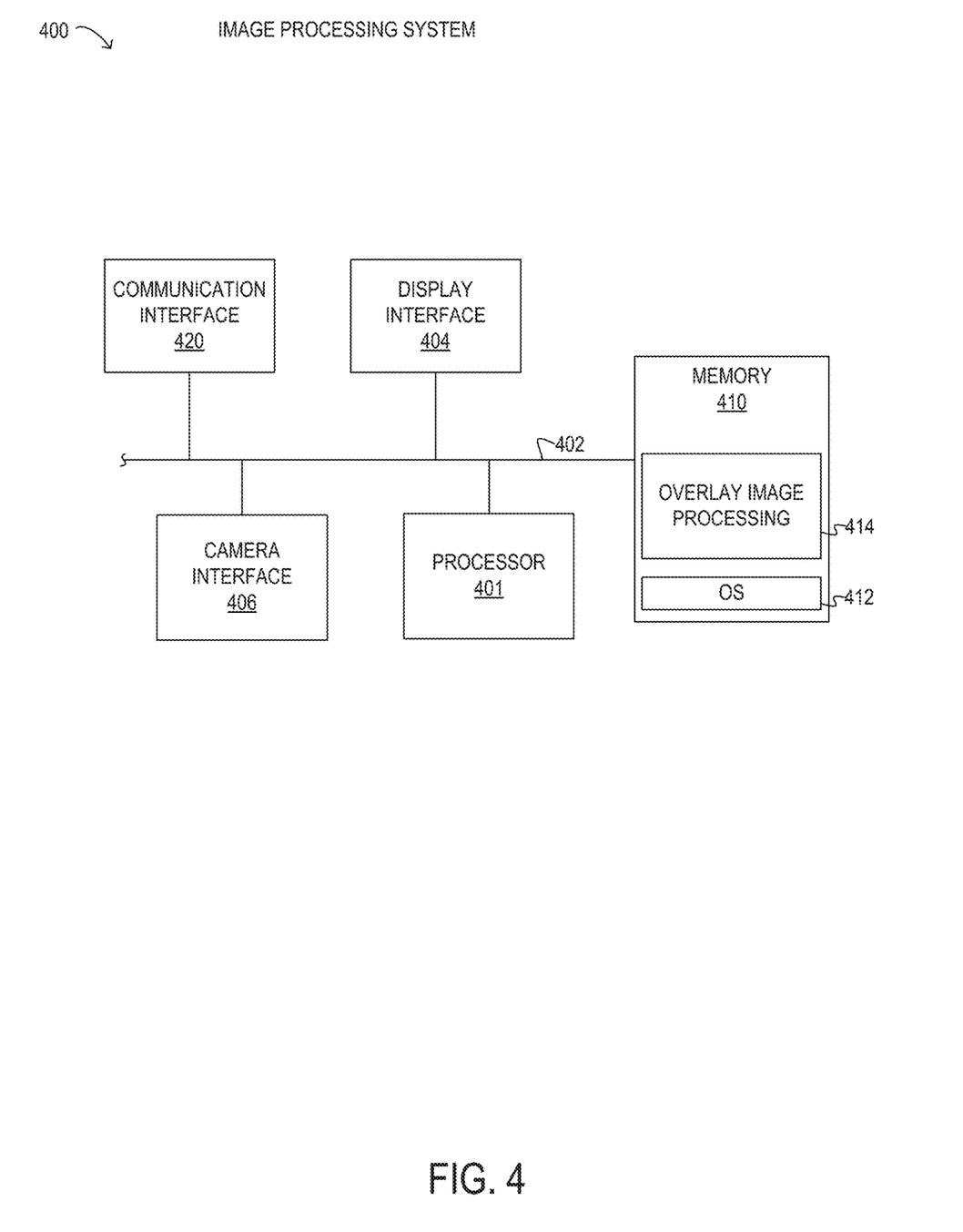
FIG. 4 is a block diagram of selected elements of an embodiment of an image processing system for overlay imaging for registration of a patient eye.

Referring now to FIG. 4, a block diagram illustrating selected elements of an embodiment of an image processing system 400 is presented. In the embodiment depicted in FIG. 4, image processing system 400 includes processor 401 coupled via shared bus 402 to memory media collectively identified as memory 410.

Image processing system 400, as depicted in FIG. 4, further includes communication interface 420 that can interface image processing system 400 to various external entities, such as a network or instrumentation bus included with a surgical laser system. In embodiments suitable for overlay imaging for registration of a patient eye for laser surgery, image processing system 400, as depicted in FIG. 4, includes display interface 404 that connects shared bus 402, or another bus, with an output port for one or more displays, such as a display of a surgical laser system, an ocular display of a surgical microscope, or another display. As shown, image processing system 400 may further include a camera interface 406 for acquisition of surgical images from a camera included in the surgical laser system. In some embodiments, camera interface 406 includes a camera and suitable optics for overlay imaging for registration of a patient eye for laser surgery.

In FIG. 4, memory 410 encompasses persistent and volatile media, fixed and removable media, and magnetic and semiconductor media. Memory 410 is operable to store instructions, data, or both. Memory 410 as shown includes sets or sequences of instructions, namely, an operating system 412, and an overlay image processing application 414. Operating system (OS) 412 may be a UNIX or UNIX-like operating system, a Windows® family operating system, or another suitable operating system.

In various embodiments, image processing system 400 may be integrated with different types of equipment. In one embodiment, image processing system 400 is integrated with a surgical microscope. The surgical microscope may be integrated within the surgical laser system.

Modifications, additions, or omissions may be made to image processing system 400 without departing from the scope of the disclosure. The components and elements of image processing system 400, as described herein, may be integrated or separated according to particular applications. Image processing system 400 may be implemented using more, fewer, or different components in some embodiments.

Figure 5:
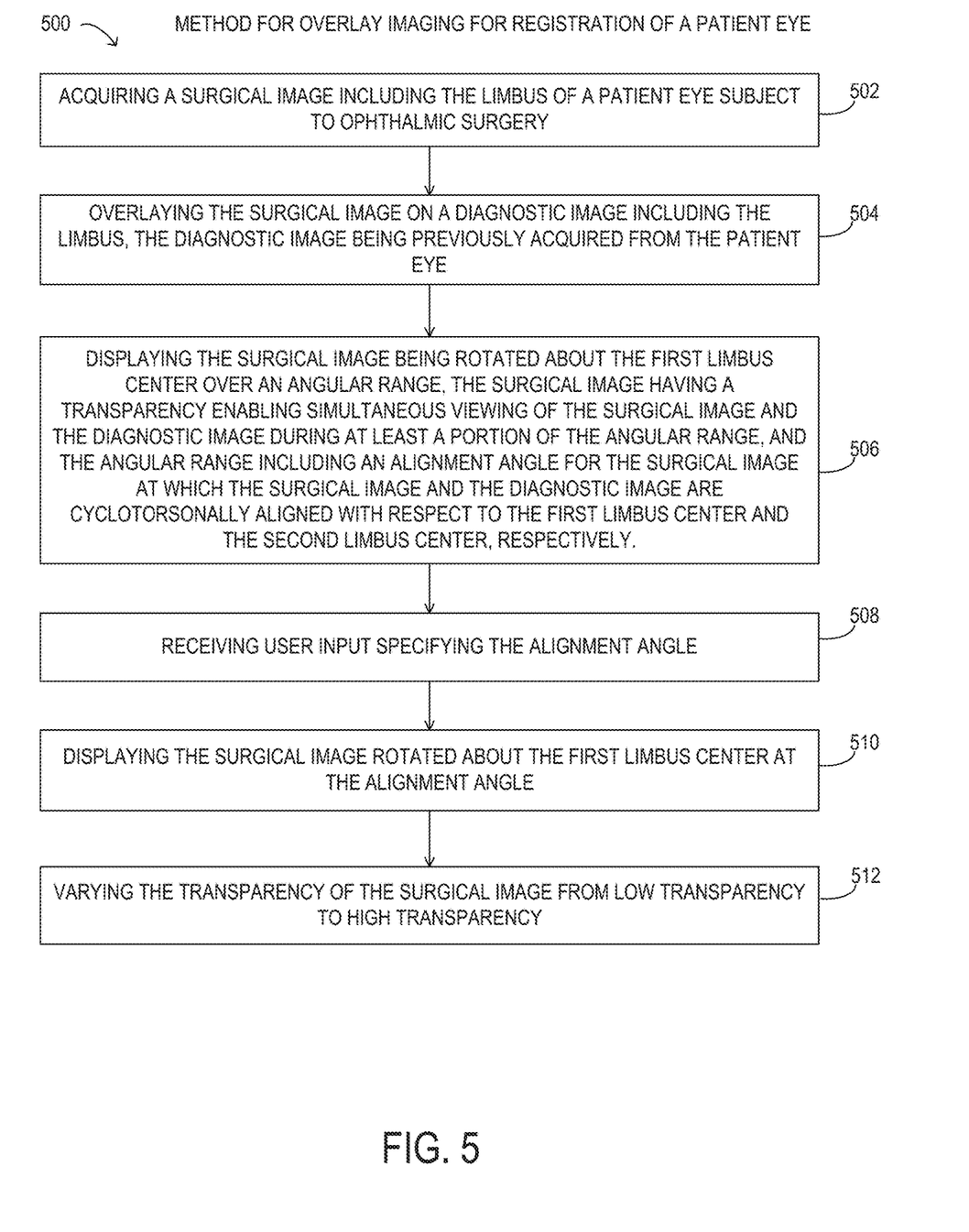
FIG. 5 is a flow chart of selected elements of a method for overlay imaging for registration of a patient eye.

Referring now to FIG. 5, a flow chart of selected elements of an embodiment of a method 500 for overlay imaging for registration of a patient eye for laser surgery, as described herein, is depicted in flowchart form. It is noted that certain operations described in method 500 may be optional or may be rearranged in different embodiments. Method 500 may be performed by overlay image processing application 414 in FIG. 4.

Method 500 may begin, at step 502, by acquiring a surgical image including the limbus of a patient eye subject to ophthalmic surgery. The ophthalmic surgery may be laser surgery. At step 504, the surgical image is overlaid on a diagnostic image including the limbus, the diagnostic image being previously acquired from the patient eye. At step 506, the surgical image is displayed being rotated about the first limbus center over an angular range, the surgical image having a transparency enabling simultaneous viewing of the surgical image and the diagnostic image during at least a portion of the angular range, and the angular range including an alignment angle for the surgical image at which the surgical image and the diagnostic image are cyclotorsonally aligned with respect to the first limbus center and the second limbus center, respectively. At step 508, user input specifying the alignment angle is received. It is noted that step 508 may be repeated or performed iteratively in conjunction with other steps in method 500. At step 510, the surgical image is displayed rotated about the first limbus center at the alignment angle. At step 512, the transparency of the surgical image is varied from low transparency to high transparency.

As disclosed herein, methods and systems for overlay imaging for registration of a patient eye for laser surgery include aligning and overlaying a surgical image of the limbus over a previously acquired diagnostic image of the limbus. The surgical image is displayed with a degree of transparency and enabled to rotate about the limbus center. Various types of colors, markers, contrast, and backgrounds may be used to generate a display for determining the alignment angle between the diagnostic image and the surgical image.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A method for registration of patient eyes for ophthalmic surgery, the method comprising:

acquiring a surgical image including a limbus of a patient eye subject to ophthalmic surgery;

overlaying the surgical image on a diagnostic image including the limbus, the diagnostic image being previously acquired from the patient eye;

aligning a first limbus center of the surgical image with a second limbus center of the diagnostic image;

determining an expected alignment angle;

displaying the surgical image being rotated about the first limbus center over an angular range centered at the expected alignment angle, wherein the surgical image has a transparency enabling simultaneous viewing of the surgical image and the diagnostic image during at least a portion of the angular range, and wherein the angular range includes an actual alignment angle for the surgical image at which the surgical image and the diagnostic image are cyclotorsonally aligned with respect to the first limbus center and the second limbus center, respectively; and displaying a first pair of reticules associated with the diagnostic image;

displaying a second pair of reticules associated with the surgical image; and displaying a numerical angle measure of the rotation of the first pair of reticules with respect to the second pair of reticules;

wherein the first pair of reticules intersect at the limbus center and the second pair of reticules intersects at the limbus center.

2. The method of claim 1, wherein the surgical image and the diagnostic image include at least a portion of an iris of the patient's eye.

3. The method of claim 1, wherein both the surgical image and the diagnostic image respectively include at least one identical marker at a common location on the patient's eye, wherein the marker on the diagnostic image and the marker of the surgical image overlap when the diagnostic image is rotationally aligned with the surgical image.

4. The method of claim 3, wherein the marker is an indication of an iris structure of an iris displayed over a uniform background in place of the iris.

5. The method of claim 3, wherein a first marker of the surgical image has a first color, and a second marker of the diagnostic image has a second color.

6. The method of claim 3, wherein the marker is a hollow shape, wherein the hollow shape is located on the diagnostic image and the corresponding hollow shape located on the surgical image appears as a single hollow shape when the diagnostic image is rotationally aligned with the surgical image.

7. The method of claim 6, wherein the hollow shape includes at least one of: a polygon and an ellipse.

8. The method of claim 1, wherein displaying the surgical image further comprises:

displaying the surgical image being incrementally rotated about the first limbus center over a step angle of rotation, in response to user input indicating the step angle.

9. The method of claim 1, further comprising:

varying the transparency of the surgical image from low transparency to high transparency.

10. The method of claim 1, further comprising receiving user input to select at least one of:

the transparency displayed;

a range of transparency from high transparency to low transparency;

a step transparency within the transparency range;

a first color in the surgical image;

a second color in the diagnostic image;

a number of markers;

a type of marker;

a location of a marker;

a contrast of the iris;

a displayed portion of the iris;

the angular range; and a step angle within the angular range.

11. An image processing system for registration of patient eyes for ophthalmic surgery, the image processing system comprising:

a processor enabled to access memory media storing instructions executable by the processor to, acquire a surgical image including a limbus of a patient eye subject to ophthalmic surgery;

overlay the surgical image on a diagnostic image including the limbus, the diagnostic image being previously acquired from the patient eye;

align a first limbus center of the surgical image with a second limbus center of the diagnostic image; and determine an expected alignment angle;

display the surgical image being rotated about the first limbus center over an angular range centered at the expected alignment angle, wherein the surgical image has a transparency enabling simultaneous viewing of the surgical image and the diagnostic image during at least a portion of the angular range, and wherein the angular range includes an actual alignment angle for the surgical image at which the surgical image and the diagnostic image are cyclotorsonally aligned with respect to the first limbus center and the second limbus center, respectively; and display a first pair of reticules associated with the diagnostic image; and display a second pair of reticules associated with the surgical image;

display a numerical angle measure of the rotation of the first pair of reticules with respect to the second pair of reticules;

wherein the first pair of reticules intersect at the limbus center and the second pair of reticules intersects at the limbus center.

12. The image processing system of claim 11, wherein the surgical image and the diagnostic image include at least a portion of an iris of the patient's eye.

13. The image processing system of claim 11, wherein both the surgical image and the diagnostic image respectively include at least one identical marker at a common location on the patient's eye, wherein the marker on the diagnostic image and the marker of the surgical image overlap when the diagnostic image is rotationally aligned with the surgical image.

14. The image processing system of claim 13, wherein the marker is an indication of an iris structure of the iris displayed over a uniform background in place of the iris.

15. The image processing system of claim 13, wherein a first marker of the surgical image has a first color, and a second marker of the diagnostic image has a second color.

16. The image processing system of claim 13, wherein the marker is a hollow shape, wherein the hollow shape located on the diagnostic image and the corresponding hollow shape located on the surgical image appears as a single hollow shape when the diagnostic image is rotationally aligned with the surgical image.

17. The image processing system of claim 16, wherein the hollow shape includes at least one of: a polygon and an ellipse.

18. The image processing system of claim 11, wherein the instructions to display the surgical image further comprise instructions to:

display the surgical image being incrementally rotated about the first limbus center over a step angle of rotation, in response to user input indicating the step angle.

19. The image processing system of claim 11, further comprising instructions to:

vary the transparency of the surgical image from low transparency to high transparency.

20. The image processing system of claim 11, further comprising instructions to receive user input to select at least one of:

the transparency displayed;
a range of transparency from high transparency to low transparency;
a step transparency within the transparency range;
a first color in the surgical image;
a second color in the diagnostic image;
a number of markers;
a type of marker;
a location of a marker;
a contrast of the iris;
a displayed portion of the iris;
the angular range; and
a step angle within the angular range.

* * * * *